(12) United States Patent
Gandhi et al.

(10) Patent No.: US 9,986,739 B2
(45) Date of Patent: Jun. 5, 2018

(54) MICROBICIDAL COMPOSITION

(71) Applicants: Dow Global Technologies LLC, Midland, MI (US); Rohm and Haas Company, Collegeville, PA (US)

(72) Inventors: Usha Gandhi, Hatboro, PA (US); Christine McInnis, Blue Bell, PA (US); Kiran Pareek, Bensalem, PA (US); Paul O. Schook, Lake Zurich, IL (US); Nigel G. Watson, Chadds Ford, PA (US); Terry Michael Williams, Lower Gwynedd, PA (US); Bei Yin, Phoenixville, PA (US)

(73) Assignees: ROHM AND HAAS COMPANY, Philadelphia, PA (US); DOW GLOBAL TECHNOLOGIES LLC, Midland, MI (US)

( * ) Notice: Subject to any disclaimer, the term of this patent is extended or adjusted under 35 U.S.C. 154(b) by 0 days. days.

(21) Appl. No.: 15/685,466

(22) Filed: Aug. 24, 2017

(65) Prior Publication Data
US 2017/0347655 A1    Dec. 7, 2017

Related U.S. Application Data

(62) Division of application No. 15/026,132, filed as application No. PCT/US2014/058953 on Oct. 3, 2014.

(60) Provisional application No. 61/886,340, filed on Oct. 3, 2013.

(51) Int. Cl.
*A01N 25/30* (2006.01)
*A01N 33/20* (2006.01)
*A01N 35/02* (2006.01)
*A01N 43/76* (2006.01)
*A01N 43/90* (2006.01)

(52) U.S. Cl.
CPC ............. *A01N 43/90* (2013.01); *A01N 25/30* (2013.01); *A01N 33/20* (2013.01); *A01N 43/76* (2013.01)

(58) Field of Classification Search
CPC ........ A01N 25/30; A01N 43/76; A01N 43/90; A01N 33/20
See application file for complete search history.

(56) References Cited

U.S. PATENT DOCUMENTS

2009/0023688 A1* 1/2009 Levy ...................... A01N 43/80 514/143
2010/0081607 A1* 4/2010 Varineau ............. B01F 17/0021 510/405

FOREIGN PATENT DOCUMENTS

WO    WO-2009155187 A1 * 12/2009 ............. C11D 1/722

* cited by examiner

*Primary Examiner* — Sarah Pihonak
(74) *Attorney, Agent, or Firm* — Kenneth Crimaldi

(57) ABSTRACT

A synergistic microbicidal composition having two components. The first component is a nonionic surfactant with structure: $R^1O(CH_2CH(CH_3)O)_5(CH_2CH_2O)_9H$, where $R^1$ is a $C_8$ alkyl group. The second component is 4,4-dimethyloxazolidine. The weight ratio of the nonionic surfactant to 4,4-dimethyloxazolidine is from 1:0.0286 to 1:0.1143 or 1:0.32 to 1:0.9143.

2 Claims, No Drawings

MICROBICIDAL COMPOSITION

This invention relates to microbicidal compositions containing cis-1-(3-chloroallyl)-3,5,7-triaza-1-azoniaadamantane chloride (CTAC), 4,4-dimethyloxazolidine (DMO) or tris(hydroxymethyl)nitromethane (Tris Nitro) and a surfactant.

A composition containing 5-chloro-2-methylisothiazolin-3-one, 2-methylisothiazolin-3-one and a nonionic dispersant is disclosed in U.S. Pat. No. 4,295,932. The composition contains a 3:1 mixture of 5-chloro-2-methylisothiazolin-3-one and 2-methylisothiazolin-3-one, and a copolymer of ethylene oxide and propylene oxide which appears to have the same composition as PLURONIC L61 or TERGITOL L61 dispersant. However, there is a need for combinations of microbicides having synergistic activity against various strains of microorganisms to provide effective control of the microorganisms. Moreover, there is a need for such combinations containing lower levels of individual microbicides for environmental and economic benefit. The problem addressed by this invention is to provide such synergistic combinations of microbicides.

STATEMENT OF THE INVENTION

The present invention is directed to a synergistic microbicidal composition comprising: (a) a nonionic surfactant with structure:

$$R^1O(CH_2CH(CH_3)O)_5(CH_2CH_2O)_9H$$

where $R^1$ is a $C_8$ alkyl group; and (b) cis-1-(3-chloroallyl)-3,5,7-triaza-1-azoniaadamantane chloride; wherein a weight ratio of said nonionic surfactant to cis-1-(3-chloroallyl)-3,5,7-triaza-1-azoniaadamantane chloride is from 1:0.2 to 1:1.1429.

The present invention is further directed to a synergistic microbicidal composition comprising: (a) a nonionic surfactant with structure:

$$R^2O(CH_2CH(CH_3)O)_3(CH_2CH_2O)_5H$$

where $R^2$ is a mixture of $C_8$-$C_{14}$ linear alkyl groups; and (b) cis-1-(3-chloroallyl)-3,5,7-triaza-1-azoniaadamantane chloride; wherein a weight ratio of said nonionic surfactant to cis-1-(3-chloroallyl)-3,5,7-triaza-1-azoniaadamantane chloride is from 1:0.04 to 1:0.9143.

The present invention is further directed to a synergistic microbicidal composition comprising: (a) a nonionic surfactant with structure:

$$R^2O(CH_2CH(CH_3)O)_3(CH_2CH_2O)_7H$$

where $R^2$ is a mixture of $C_8$-$C_{14}$ linear alkyl groups; and (b) cis-1-(3-chloroallyl)-3,5,7-triaza-1-azoniaadamantane chloride; wherein a weight ratio of said nonionic surfactant to cis-1-(3-chloroallyl)-3,5,7-triaza-1-azoniaadamantane chloride is from 1:0.016 to 1:0.0571.

The present invention is further directed to a synergistic microbicidal composition comprising: (a) a nonionic surfactant with structure:

$$R^1O(CH_2CH(CH_3)O)_5(CH_2CH_2O)_9H$$

where $R^1$ is a $C_8$ alkyl group; and (b) 4,4-dimethyloxazolidine; wherein a weight ratio of said nonionic surfactant to 4,4-dimethyloxazolidine is from 1:0.0286 to 1:0.1143 or 1:0.32 to 1:0.9143.

The present invention is further directed to a synergistic microbicidal composition comprising: (a) a nonionic surfactant with structure:

$$R^2O(CH_2CH(CH_3)O)_3(CH_2CH_2O)_5H$$

where $R^2$ is a mixture of $C_8$-$C_{14}$ linear alkyl groups; and (b) 4,4-dimethyloxazolidine; wherein a weight ratio of said nonionic surfactant to 4,4-dimethyloxazolidine is from 1:0.06 to 1:0.6857.

The present invention is further directed to a synergistic microbicidal composition comprising: (a) a nonionic surfactant with structure:

$$R^2O(CH_2CH(CH_3)O)_3(CH_2CH_2O)_7H$$

where $R^2$ is a mixture of $C_8$-$C_{14}$ linear alkyl groups; and (b) 4,4-dimethyloxazolidine; wherein a weight ratio of said nonionic surfactant to 4,4-dimethyloxazolidine is from 1:0.024 to 1:0.2743.

The present invention is further directed to a synergistic microbicidal composition comprising: (a) a nonionic surfactant with structure:

$$R^2O(CH_2CH(CH_3)O)_3(CH_2CH_2O)_7H$$

where $R^2$ is a mixture of $C_8$-$C_{14}$ linear alkyl groups; and (b) tris(hydroxymethyl)nitromethane; wherein a weight ratio of said nonionic surfactant to tris(hydroxymethyl)nitromethane is from 1:0.16 to 1:1.8286.

The present invention is further directed to methods for inhibiting the growth of microorganisms in aqueous media by adding to an aqueous medium a nonionic surfactant as described herein and cis-1-(3-chloroallyl)-3,5,7-triaza-1-azoniaadamantane chloride, 4,4-dimethyloxazolidine or tris(hydroxymethyl)nitromethane in the ratios described herein.

DETAILED DESCRIPTION OF THE INVENTION

"CTAC" is cis-1-(3-chloroallyl)-3,5,7-triaza-adamantane chloride, CAS No. 51229-78-8, "DMO" is 4,4-dimethyloxazolidine, CAS No. 51200-87-4, and "Tris Nitro" is tris(hydroxymethyl)nitromethane, CAS No. 126-11-4. As used herein, the following terms have the designated definitions, unless the context clearly indicates otherwise. The term "microbicide" refers to a compound capable of inhibiting the growth of or controlling the growth of microorganisms; microbicides include bactericides, fungicides and algaecides. The term "microorganism" includes, for example, fungi (such as yeast and mold), bacteria and algae. The following abbreviations are used throughout the specification: ppm=parts per million by weight (weight/weight), mL=milliliter. Unless otherwise specified, temperatures are in degrees centigrade (° C.), references to percentages are percentages by weight (wt %) and amounts and ratios are on an active ingredient basis, i.e., total weight of CTAC and the nonionic surfactant. Numbers of polymerized units of propylene oxide or ethylene oxide are number averages.

Preferably, the weight ratio of the nonionic surfactant with structure:

$$R^1O(CH_2CH(CH_3)O)_5(CH_2CH_2O)_9H$$

where $R^1$ is a $C_8$ alkyl group to CTAC is from 1:0.2857 to 1:1.1429, preferably from 1:0.5714 to 1:1.1429. Preferably, the weight ratio of the nonionic surfactant with structure:

$$R^2O(CH_2CH(CH_3)O)_3(CH_2CH_2O)_5H$$

where $R^2$ is a mixture of $C_8$-$C_{14}$ linear alkyl groups to CTAC is from 1:0.0457 to 1:0.9143.

The present invention is further directed to a method for inhibiting the growth of S. aureus, in an aqueous medium by adding: (a) a nonionic surfactant with structure:

$$R^2O(CH_2CH(CH_3)O)_3(CH_2CH_2O)_5H$$

where $R^2$ is a mixture of $C_8$-$C_{14}$ linear alkyl groups; and (b) CTAC; wherein a weight ratio of said nonionic surfactant to CTAC is from 1:0.0457 to 1:0.9143.

The present invention is further directed to a method for inhibiting the growth of S. aureus, in an aqueous medium by adding: (a) a nonionic surfactant with structure:

$$R^2O(CH_2CH(CH_3)O)_3(CH_2CH_2O)_7H$$

where $R^2$ is a mixture of $C_8$-$C_{14}$ linear alkyl groups; and (b) Tris Nitro; wherein a weight ratio of said nonionic surfactant to Tris Nitro is from 1:0.16 to 1:1.8286.

$R^2$ is a mixture of $C_8$-$C_{14}$ linear alkyl groups. Preferably, the $C_8$-$C_{14}$ linear alkyl groups comprise from 50 to 85 wt % $C_8$-$C_{10}$ linear alkyl groups and 15 to 50 wt % $C_{12}$-$C_{14}$ linear alkyl groups, preferably from 60 to 75 wt % $C_8$-$C_{10}$ linear alkyl groups and 25 to 40 wt % $C_{12}$-$C_{14}$ linear alkyl groups, preferably about 70 wt % $C_8$-$C_{10}$ linear alkyl groups and about 30 wt % $C_{12}$-$C_{14}$ linear alkyl groups. Preferably, the linear alkyl groups are derived from seed oil. Preferably, $R^1$ is 2-ethylhexyl.

Preferably, each of the compositions is substantially free of microbicides other than the nonionic surfactant and CTAC, DMO or Tris Nitro, i.e., it has less than 1 wt % of microbicides other than the nonionic surfactant and CTAC, DMO or Tris Nitro based on total weight of active ingredients, preferably less than 0.5 wt %, preferably less than 0.2 wt %, preferably less than 0.1 wt %. Preferably, when the nonionic surfactant and CTAC, DMO or Tris Nitro are added to an aqueous medium, the medium is substantially free of other microbicides, i.e., it has less than 1 wt % of microbicides other than the nonionic surfactant and CTAC, DMO or Tris Nitro based on total weight of active ingredients, preferably less than 0.5 wt %, preferably less than 0.2 wt %, preferably less than 0.1 wt %.

The compositions of this invention may contain other ingredients, e.g., defoamers and emulsifiers. The microbicidal compositions of the present invention can be used to inhibit the growth of microorganisms or higher forms of aquatic life (such as protozoans, invertebrates, bryozoans, dinoflagellates, crustaceans, mollusks, etc) by introducing a microbicidally effective amount of the compositions into an aqueous medium subject to microbial attack. Suitable aqueous media are found in, for example: industrial process water; electrocoat deposition systems; cooling towers; air washers; gas scrubbers; mineral slurries; wastewater treatment; ornamental fountains; reverse osmosis filtration; ultrafiltration; ballast water; evaporative condensers; heat exchangers; pulp and paper processing fluids and additives; starch; plastics; emulsions; dispersions; paints; latices; coatings, such as varnishes; construction products, such as mastics, caulks, and sealants; construction adhesives, such as ceramic adhesives, carpet backing adhesives, and laminating adhesives; industrial or consumer adhesives; photographic chemicals; printing fluids; household products, such as bathroom and kitchen cleaners; cosmetics; toiletries; shampoos; soaps; personal care products such as wipes, lotions, sunscreen, conditioners, creams, and other leave-on applications; detergents; industrial cleaners; floor polishes; laundry rinse water; metalworking fluids; conveyor lubricants; hydraulic fluids; leather and leather products; textiles; textile products; wood and wood products, such as plywood, chipboard, flakeboard, laminated beams, oriented strandboard, hardboard, and particleboard; petroleum processing fluids; fuel; oilfield fluids, such as injection water, fracture fluids, and drilling muds; agriculture adjuvant preservation; surfactant preservation; medical devices; diagnostic reagent preservation; food preservation, such as plastic or paper food wrap; food, beverage, and industrial process pasteurizers; toilet bowls; recreational water; pools; and spas.

The specific amount of the microbicidal compositions of this invention necessary to inhibit or control the growth of microorganisms in an application will vary. Typically, the amount of the composition of the present invention is sufficient to control the growth of microorganisms if it provides from 300 to 10,000 ppm (parts per million) active ingredients of the composition. It is preferred that the active ingredients (i.e., nonionic surfactant and CTAC, DMO or Tris Nitro) of the composition be present in the medium to be treated in an amount of at least 500 ppm, preferably at least 600 ppm, preferably at least 800 ppm. It is preferred that the active ingredients of the composition be present in the locus in an amount of no more than 6,000 ppm, preferably no more than 5,000 ppm, preferably no more than 4,000 ppm, preferably no more than 3,000 ppm, preferably no more than 2,500 ppm, preferably no more than 2,000 ppm. In a method of this invention, a composition is treated to inhibit microbial growth by adding, together or separately, the nonionic surfactant and CTAC, DMO or Tris Nitro, in amounts that would produce the concentrations indicated above.

EXAMPLES

Surfactants and biocides were evaluated for synergy by determining the synergy index (S.I.) of the combination. Synergy index was calculated based on minimum inhibitory concentrations (MIC) of two antimicrobial compounds (A and B) alone and in combinations. The tests organisms were Gram negative bacteria (Pseudomonas aeruginosa ATCC #15442), Gram positive bacteria (Staphylococcus aureus ATCC #6538), yeast (Candida albicans ATCC#10203) and mold (Aspergillus niger ATCC#16404). Contact time for the bacteria was 24 and 48 hours, yeast was 48 and 72 hrs, and 3 and 7 days for mold. The test was carried out in 96 well microtiter plates.

Surf. A $R^1O(CH_2CH(CH_3)O)_5(CH_2CH_2O)_9H$, where $R^1$ is 2-ethylhexyl
Surf. D $R^2O(CH_2CH(CH_3)O)_3(CH_2CH_2O)_5H$
Surf. E $R^2O(CH_2CH(CH_3)O)_3(CH_2CH_2O)_7H$
In Surf. D and Surf. E, $R^2$ is a mixture of $C_8$-$C_{14}$ linear alkyl groups (70% $C_8$-$C_{10}$ linear alkyl and 30% $C_{12}$-$C_{14}$ linear alkyl)

| | Inoculums Used Inoculum Size of organisms ( CFU/ml ) | | | |
|---|---|---|---|---|
| Surfactants | Staphylococcus aureus ATCC# 6538 | Pseudomonas aeruginosa ATCC # 15442 | Aspergillus niger ATCC# 16404 | Candida albicans ATCC#10203 |
| Surf. A | 1.156E+06 | 8.134E+07 | 1.156E+06 | 1.156 + 06 |
| Surf. D | 1.808E+05 | 1.156E+08 | 1.156E+06 | 5.726E+05 |
| Surf. E | 1.808E+06 | 5.727E+07 | 5.726E+05 | 1.808E+06 |

TABLE 4

| Media Used Media Used for testing | | | |
|---|---|---|---|
| *Staphylococcus aureus* ATCC# 6538 | *Pseudomonas aeruginosa* ATCC # 15442 | *Aspergillus niger* ATCC# 16404 | *Candida albicans* ATCC#10203 |
| 10% Tryptic soy broth | 10% Tryptic soy broth | Potato dextrose broth | Potato dextrose broth |

The pH of the Triptic soy broth was 7.3 and the Potato dextrose broth was 5.1.

The test results for demonstration of synergy of the MIC combinations are shown in the tables below. Each table shows the results for combinations of two components against the microorganisms tested with incubation times; the end-point activity in ppm measured by the MIC for compound A alone (CA), for component B alone (CB), and the mixture (Ca) and (Cb); the calculated SI value; and the range of synergistic ratios for each combination tested. SI is calculated as follows:

$$Ca/CA + Cb/CB = \text{Synergy Index (“SI”)}$$

Wherein:
CA=concentration of compound A in ppm, acting alone, which produced an end point (MIC of Compound A).
Ca=concentration of compound A in ppm, in the mixture, which produced an end point.
CB=concentration of compound B in ppm, acting alone, which produced an end point (MIC of Compound B).
Cb=concentration of compound B in ppm, in the mixture, which produced an end point.

When the sum of Ca/CA and Cb/CB is greater than one, antagonism is indicated. When the sum is equal to one, additivity is indicated, and when less than one, synergism is demonstrated.

The ratio ranges at which CTAC, DMO or Tris Nitro and the surfactants were tested are as summarized in the following tables:

| CTAC with Surf. A | | | | |
|---|---|---|---|---|
| Organism | ATCC# | From | To | Ratio Range |
| *Staphylococcus aureus* | 6538 | 0.2:20,000 | 1,000:218.75 | 1:0.00001-1:4.5714 |
| *Aspergillus niger* | 16404 | 0.2:20,000 | 1,000:218.75 | 1:0.00001-1:4.5714 |
| *Candida albicans* | 10203 | 0.2:20,000 | 1,000:218.75 | 1:0.00001-1:4.5714 |
| *Pseudomonas aeruginosa* | 15442 | 0.2:20,000 | 1,000:218.75 | 1:0.00001-1:4.5714 |

| CTAC with Surf. E | | | | |
|---|---|---|---|---|
| Organism | ATCC# | From | To | Ratio Range |
| *Staphylococcus aureus* | 6538 | 0.2:20,000 | 1,000:218.75 | 1:0.00001-1:4.5714 |
| *Aspergillus niger* | 16404 | 2.0:20,000 | 10,000:218.75 | 1:0.0001-1:45.7143 |
| *Candida albicans* | 10203 | 2.0:20,000 | 10,000:218.75 | 1:0.0001-1:45.7143 |
| *Pseudomonas aeruginosa* | 15442 | 0.2:20,000 | 1,000:218.75 | 1:0.00001-1:4.5714 |

| CTAC with Surf. D | | | | |
|---|---|---|---|---|
| Organism | ATCC# | From | To | Ratio Range |
| *Staphylococcus aureus* | 6538 | 0.2:20,000 | 1,000:218.75 | 1:0.00001-1:4.5714 |
| *Aspergillus niger* | 16404 | 0.2:20,000 | 1,000:218.75 | 1:0.00001-1:4.5714 |
| *Candida albicans* | 10203 | 0.2:20,000 | 1,000:218.75 | 1:0.00001-1:4.5714 |
| *Pseudomonas aeruginosa* | 15442 | 0.2:20,000 | 1,000:218.75 | 1:0.00001-1:4.5714 |

| DMO with Surf. A | | | | |
|---|---|---|---|---|
| Organism | ATCC# | From | To | Ratio Range |
| *Staphylococcus aureus* | 6538 | 0.2:20,000 | 1,000:218.75 | 1:0.00001-1:4.5714 |
| *Aspergillus niger* | 16404 | 0.2:20,000 | 1,000:218.75 | 1:0.00001-1:4.5714 |
| *Candida albicans* | 10203 | 0.2:20,000 | 1,000:218.75 | 1:0.00001-1:4.5714 |
| *Pseudomonas aeruginosa* | 15442 | 0.2:20,000 | 1,000:218.75 | 1:0.00001-1:4.5714 |

| DMO with Surf. E | | | | |
|---|---|---|---|---|
| Organism | ATCC# | From | To | Ratio Range |
| *Staphylococcus aureus* | 6538 | 0.2:20,000 | 1,000:218.75 | 1:0.00001-1:4.5714 |
| *Aspergillus niger* | 16404 | 0.2:20,000 | 1,000:218.75 | 1:0.00001-1:4.5714 |
| *Candida albicans* | 10203 | 0.2:20,000 | 1,000:218.75 | 1:0.00001-1:4.5714 |
| *Pseudomonas aeruginosa* | 15442 | 0.2:20,000 | 1,000:218.75 | 1:0.00001-1:4.5714 |

| DMO with Surf. D | | | | |
|---|---|---|---|---|
| Organism | ATCC# | From | To | Ratio Range |
| *Staphylococcus aureus* | 6538 | 0.2:20,000 | 1,000:218.75 | 1:0.00001-1:4.5714 |
| *Aspergillus niger* | 16404 | 0.2:20,000 | 1,000:218.75 | 1:0.00001-1:4.5714 |
| *Candida albicans* | 10203 | 0.2:20,000 | 1,000:218.75 | 1:0.00001-1:4.5714 |
| *Pseudomonas aeruginosa* | 15442 | 0.2:20,000 | 1,000:218.75 | 1:0.00001-1:4.5714 |

| TrisNitro with Surf. A | | | | |
|---|---|---|---|---|
| Organism | ATCC# | From | To | Ratio Range |
| *Staphylococcus aureus* | 6538 | 0.2:20,000 | 1,000:218.75 | 1:0.00001-1:4.5714 |
| *Aspergillus niger* | 16404 | 0.02:20,000 | 100:218.75 | 1:0.000001-1:0.45714 |
| *Candida albicans* | 10203 | 0.2:20,000 | 1,000:218.75 | 1:0.00001-1:4.5714 |
| *Pseudomonas aeruginosa* | 15442 | 0.2:20,000 | 1,000:218.75 | 1:0.00001-1:4.5714 |

| TrisNitro with Surf. E | | | | |
|---|---|---|---|---|
| Organism | ATCC# | From | To | Ratio Range |
| *Staphylococcus aureus* | 6538 | 0.2:20,000 | 1,000:218.75 | 1:0.00001-1:4.5714 |
| *Aspergillus niger* | 16404 | 0.2:20,000 | 1,000:218.75 | 1:0.00001-1:4.5714 |
| *Candida albicans* | 10203 | 0.2:20,000 | 1,000:218.75 | 1:0.00001-1:4.5714 |
| *Pseudomonas aeruginosa* | 15442 | 0.2:20,000 | 1,000:218.75 | 1:0.00001-1:4.5714 |

| TrisNitro with Surf. D | | | | |
|---|---|---|---|---|
| Organism | ATCC# | From | To | Ratio Range |
| *Staphylococcus aureus* | 6538 | 0.2:20,000 | 1,000:218.75 | 1:0.00001-1:4.5714 |
| *Aspergillus niger* | 16404 | 0.2:20,000 | 1,000:218.75 | 1:0.00001-1:4.5714 |
| *Candida albicans* | 10203 | 0.2:20,000 | 1,000:218.75 | 1:0.00001-1:4.5714 |
| *Pseudomonas aeruginosa* | 15442 | 0.2:20,000 | 1,000:218.75 | 1:0.00001-1:4.5714 |

A: Surf. A
B: CTAC
Media: PDB
Inoculum size: 1.156E+06

| | | |
|---|---|---|
| *A. niger* | ATCC#16404 | No Synergy |
| *C. albicans* | ATCC#10203 | No Synergy |

A: Surf. A
B: CTAC
Media: 1/10 TSB
Inoculum size: 1.156E+06

| | | |
|---|---|---|
| *S. aureus* | ATCC#6538 | No Synergy |

A: Surf. A
B: CTAC
Media: 1/10 TSB
Inoculum size: 1.156E+06

PPM AI MIC Values
($3^{rd}$ Day)

| Test Organism | Alone | | Combination | | | Ratio |
|---|---|---|---|---|---|---|
| | CA | CB | Ca | Cb | S.I. | (Ca:Cb) |
| *P. aeruginosa* | >20000 | 600 | 20000 | 500 | <1.83 | 1:0.0250 |
| ATCC#15442 | >20000 | 600 | 10000 | 500 | <1.33 | 1:0.0500 |
| | >20000 | 600 | 5000 | 500 | <1.08 | 1:0.1000 |
| | >20000 | 600 | 2500 | 500 | <0.96 | 1:0.2000 |
| | >20000 | 600 | 1750 | 500 | <0.92 | 1:0.2857 |
| | >20000 | 600 | 875 | 500 | <0.88 | 1:0.5714 |
| | >20000 | 600 | 437.5 | 500 | <0.86 | 1:1.1429 |

A: Surf. D
B: CTAC
Media: PDB
Inoculum size: 1.156E+06

PPM AI MIC Values
(3rd day)

| Test Organism | Alone | | Combination | | | Ratio |
|---|---|---|---|---|---|---|
| | CA | CB | Ca | Cb | S.I. | (Ca:Cb) |
| *A. niger* | >20000 | 1000 | 10000 | 600 | <1.10 | 1:0.0600 |
| | >20000 | 1000 | 10000 | 800 | <1.30 | 1:0.0800 |
| ATCC#16404 | >20000 | 1000 | 5000 | 800 | <1.05 | 1:0.1600 |
| | >20000 | 1000 | 2500 | 800 | <0.93 | 1:0.3200 |
| | >20000 | 1000 | 1750 | 800 | <0.89 | 1:0.4571 |
| | >20000 | 1000 | 875 | 800 | <0.84 | 1:0.9143 |

A: Surf. D
B: CTAC
Media: PDB
Inoculum size: 5.726E+05 CFU/ml

PPM AI MIC Values
(48 hrs)

| Test Organism | Alone | | Combination | | | Ratio |
|---|---|---|---|---|---|---|
| | CA | CB | Ca | Cb | S.I. | (Ca:Cb) |
| *C. albicans* | >20000 | 1000 | 10000 | 400 | <0.90 | 1:0.0400 |
| ATCC#10203 | >20000 | 1000 | 10000 | 500 | <1.00 | 1:0.0500 |
| | >20000 | 1000 | 10000 | 600 | <1.10 | 1:0.0600 |
| | >20000 | 1000 | 10000 | 800 | <1.30 | 1:0.0800 |
| | >20000 | 1000 | 5000 | 400 | <0.65 | 1:0.0800 |
| | >20000 | 1000 | 5000 | 500 | <0.75 | 1:0.1000 |
| | >20000 | 1000 | 5000 | 600 | <0.85 | 1:0.1200 |
| | >20000 | 1000 | 5000 | 800 | <1.05 | 1:0.1600 |

A: Surf. D
B: CTAC
Media: 1/10 TSB
Inoculum size: 1.808E+05

PPM AI MIC Values
(24 hrs)

| Test Organism | Alone | | Combination | | | Ratio |
|---|---|---|---|---|---|---|
| | CA | CB | Ca | Cb | S.I. | (Ca:Cb) |
| *S. aureus* | >20000 | 300 | 10000 | 80 | <0.77 | 1:0.0080 |
| ATCC# 6538 | >20000 | 300 | 10000 | 100 | <0.83 | 1:0.0100 |
| | >20000 | 300 | 10000 | 200 | <1.17 | 1:0.0200 |
| | >20000 | 300 | 5000 | 200 | <0.92 | 1:0.0400 |
| | >20000 | 300 | 5000 | 80 | <0.52 | 1:0.0160 |
| | >20000 | 300 | 5000 | 100 | <0.58 | 1:0.0200 |
| | >20000 | 300 | 1750 | 80 | <0.35 | 1:0.0457 |
| | >20000 | 300 | 1750 | 100 | <0.42 | 1:0.0571 |
| | >20000 | 300 | 1750 | 200 | <0.75 | 1:0.1143 |
| | >20000 | 300 | 875 | 200 | <0.71 | 1:0.2286 |

A: Surf. D
B: CTAC
Media: 1/10 TSB
Inoculum size: 1.808E+05

PPM AI MIC Values
(24 hrs)

| Test Organism | Alone | | Combination | | | Ratio |
|---|---|---|---|---|---|---|
| | CA | CB | Ca | Cb | S.I. | (Ca:Cb) |
| | >20000 | 300 | 437.5 | 200 | <0.69 | 1:0.9143 |
| | >20000 | 300 | 218.75 | 200 | <0.68 | 1:0.2286 |

A: Surf. D
B: CTAC
Media: 1/10 TSB
Inoculum size: 1.156E+06

| P. aeruginosa | ATCC#15442 | No Synergy |
|---|---|---|

A: Surf. E
B: CTAC
Media: PDB
Inoculum 1.808E+05

| A. niger | ATCC 16404 | No synergy |
|---|---|---|

A: Surf. E
B: CTAC
Media: PDB
Inoculum 1.808E+05

PPM AI MIC Values
(48 hrs)

| Test Organism | Alone | | Combination | | | Ratio |
|---|---|---|---|---|---|---|
| | CA | CB | Ca | Cb | S.I. | (Ca:Cb) |
| C. albicans ATCC 10203 | >20000 | 2997 | 10000 | 1999 | <1.17 | 1:0.1999 |

A: Surf. E
B: CTAC
Media: 1/10 TSB
Inoculum size: 5.72E+07

| P. aeruginosa | ATCC# 15442 | No synergy |
|---|---|---|

A: Surf. E
B: CTAC
Media: 1/10 TSB
Inoculum size: 1.8E+06

PPM AI MIC Values
(24 hrs)

| Test Organism | Alone | | Combination | | | Ratio |
|---|---|---|---|---|---|---|
| | CA | CB | Ca | Cb | S.I. | (Ca:Cb) |
| S. aureus ATCC# 6538 | >20000 | 200 | 10000 | 80 | <0.90 | 1:0.0080 |
| | >20000 | 200 | 10000 | 100 | <1.00 | 1:0.0100 |
| | >20000 | 200 | 5000 | 80 | <0.65 | 1:0.0160 |
| | >20000 | 200 | 5000 | 100 | <0.75 | 1:0.0200 |
| | >20000 | 200 | 2500 | 100 | <0.63 | 1:0.0400 |
| | >20000 | 200 | 1750 | 100 | <0.59 | 1:0.0571 |

A: Surf. A
B: Tris Nitro
No synergy:
S. aureus, A. niger, C. albicans, Ps. aeruginosa A: Surf. D
B: TrisNitro
Media: 1/10 TSB
Inoculum size: 1.16E+08

PPM AI MIC Values
(24 hrs)

| Test Organism | Alone | | Combination | | | Ratio |
|---|---|---|---|---|---|---|
| | CA | CB | Ca | Cb | S.I. | (Ca:Cb) |
| Ps. aeruginosa ATCC#15442 | >20000 | 800 | 20000 | 1000 | <2.25 | 1:0.0500 |
| | >20000 | 800 | 10000 | 1000 | <1.75 | 1:0.1000 |
| | >20000 | 800 | 5000 | 1000 | <1.50 | 1:0.2000 |
| | >20000 | 800 | 2500 | 800 | <1.13 | 1:0.3200 |
| | >20000 | 800 | 1750 | 1000 | <1.34 | 1:0.5714 |
| | >20000 | 800 | 875 | 800 | <1.04 | 1:0.9143 |
| | >20000 | 800 | 437.5 | 600 | <0.77 | 1:1.3714 |
| | >20000 | 800 | 437.5 | 800 | <1.02 | 1:1.8286 |
| | >20000 | 800 | 218.75 | 800 | <1.01 | 1:3.6571 |

No synergy: S. aureus, A. niger, C. albicans

A: Surf. E
B: TrisNitro
Media: 1/10TSB
Inoculum size: 5.727E+07 CFU/ml

PPM AI MIC Values
(24 hrs)

| Test Organism | Alone | | Combination | | | Ratio |
|---|---|---|---|---|---|---|
| | CA | CB | Ca | Cb | S.I. | (Ca:Cb) |
| Ps. aeruginosa ATCC#15442 | >20000 | 1000 | 20000 | 1000 | <2.00 | 1:0.0500 |
| | >20000 | 1000 | 10000 | 1000 | <1.50 | 1:0.1000 |
| | >20000 | 1000 | 5000 | 1000 | <1.25 | 1:0.2000 |
| | >20000 | 1000 | 2500 | 1000 | <1.13 | 1:0.4000 |
| | >20000 | 1000 | 1750 | 1000 | <1.09 | 1:0.5714 |

A: Surf. E
B: TrisNitro
Media: 1/10TSB
Inoculum size: 5.727E+07 CFU/ml

PPM AI MIC Values
(24 hrs)

| Test Organism | Alone | | Combination | | | Ratio |
|---|---|---|---|---|---|---|
| | CA | CB | Ca | Cb | S.I. | (Ca:Cb) |
| | >20000 | 1000 | 875 | 1000 | <1.04 | 1:1.1429 |
| | >20000 | 1000 | 437.5 | 800 | <0.82 | 1:1.8286 |
| | >20000 | 1000 | 437.5 | 1000 | <1.02 | 1:2.2857 |
| | >20000 | 1000 | 218.75 | 800 | <0.81 | 1:3.6571 |
| | >20000 | 1000 | 218.75 | 1000 | <1.01 | 1:4.5714 |

A: Surf. E
B: TrisNitro
Media: 1/10TSB
Inoculum size: 1.808E+06 CFU/ml

PPM AI MIC Values
(24 hrs)

| Test Organism | Alone | | Combination | | | Ratio |
|---|---|---|---|---|---|---|
| | CA | CB | Ca | Cb | S.I. | (Ca:Cb) |
| S. aureus ATCC# 6538 | >20000 | 500 | 20000 | 500 | <2.00 | 1:0.0250 |
| | >20000 | 500 | 10000 | 400 | <1.30 | 1:0.0400 |
| | >20000 | 500 | 5000 | 400 | <1.05 | 1:0.0800 |
| | >20000 | 500 | 2500 | 400 | <0.93 | 1:0.1600 |
| | >20000 | 500 | 1750 | 300 | <0.69 | 1:0.1714 |
| | >20000 | 500 | 1750 | 400 | <0.89 | 1:0.2286 |
| | >20000 | 500 | 875 | 400 | <0.84 | 1:0.4571 |
| | >20000 | 500 | 437.5 | 400 | <0.82 | 1:0.9143 |
| | >20000 | 500 | 218.75 | 400 | <0.81 | 1:1.8286 |
| | >20000 | 500 | 218.75 | 500 | <1.01 | 1:2.2857 |

No synergy: *A. niger, C. albicans*

A: Surf. A
B: DMO
Media: PDB
Inoculum size: 1.156E+06 CFU/ml

PPM AI MIC Values
(3rd Day)

| Test Organism | Alone | | Combination | | | Ratio |
|---|---|---|---|---|---|---|
| | CA | CB | Ca | Cb | S.I. | (Ca:Cb) |
| *A. niger* ATCC#16404 | >20000 | 60 | 10000 | 50 | <1.33 | 1:0.0050 |
| | >20000 | 60 | 5000 | 50 | <1.08 | 1:0.0100 |
| | >20000 | 60 | 2500 | 50 | <0.96 | 1:0.0200 |
| | >20000 | 60 | 1750 | 50 | <0.92 | 1:0.0286 |

A: Surf. A
B: DMO
Media: PDB
Inoculum size: 1.156E+06 CFU/ml

PPM AI MIC Values
(3rd Day)

| Test Organism | Alone | | Combination | | | Ratio |
|---|---|---|---|---|---|---|
| | CA | CB | Ca | Cb | S.I. | (Ca:Cb) |
| | >20000 | 60 | 875 | 50 | <0.88 | 1:0.0571 |
| | >20000 | 60 | 437.5 | 50 | <0.86 | 1:0.1143 |

A: Surf. A
B: DMO
Media: PDB
Inoculum size: 1.156E+06 CFU/ml

PPM AI MIC Values
(3rd Day)

| Test Organism | Alone | | Combination | | | Ratio |
|---|---|---|---|---|---|---|
| | CA | CB | Ca | Cb | S.I. | (Ca:Cb) |
| *C. albicans* ATCC#10231 | >20000 | 1000 | 10000 | 800 | <1.30 | 1:0.0800 |
| | >20000 | 1000 | 5000 | 800 | <1.05 | 1:0.1600 |
| | >20000 | 1000 | 2500 | 800 | <0.93 | 1:0.3200 |
| | >20000 | 1000 | 875 | 800 | <0.84 | 1:0.9143 |

A: Surf. A
B: DMO
Media: 1/10 TSB
Inoculum size: 8.134 + 07 CFU/ml

PPM AI MIC Values
(24 hrs)

| Test Organism | Alone | | Combination | | | Ratio |
|---|---|---|---|---|---|---|
| | CA | CB | Ca | Cb | S.I. | (Ca:Cb) |
| *P. aeruginosa* ATCC#15442 | >20000 | 80 | 20000 | 60 | <1.75 | 1:0.0030 |

A: Surf. A
B: DMO
Media: 1/10 TSB
Inoculum size: 1.156E+06 CFU/ml

PPM AI MIC Values
(24 hrs)

| Test Organism | Alone | | Combination | | | Ratio |
|---|---|---|---|---|---|---|
| | CA | CB | Ca | Cb | S.I. | (Ca:Cb) |
| S. aureua ATCC#6538 | >20000 | 50 | 20000 | 40 | <1.80 | 1:0.0020 |

A: Surf. D
B: DMO
Media: 1/10 TSB
Inoculum size: 1.16E+08

| P. aeruginosa | ATCC#15442 | No Synergy |
|---|---|---|

A: Surf. D
B: DMO
Media: PDB
Inoculum size: 1.156E+06

PPM AI MIC Values
(3rd day)

| Test Organism | Alone | | Combination | | | Ratio |
|---|---|---|---|---|---|---|
| | CA | CB | Ca | Cb | S.I. | (Ca:Cb) |
| A. niger ATCC#16404 | >20000 | 400 | 10000 | 300 | <1.25 | 1:0.0300 |
| | >20000 | 400 | 5000 | 300 | <1.0 | 1:0.0600 |
| | >20000 | 400 | 437.5 | 300 | <0.77 | 1:0.6857 |

A: Surf. D
B: DMO
Media: PDB
Inoculum size: 5.726E+05 CFU/ml

PPM AI MIC Values
(48 hrs)

| Test Organism | Alone | | Combination | | | Ratio |
|---|---|---|---|---|---|---|
| | CA | CB | Ca | Cb | S.I. | (Ca:Cb) |
| C. albicans ATCC#10231 | >20000 | 1000 | 10000 | 800 | <1.30 | 1:0.0800 |
| | >20000 | 1000 | 5000 | 800 | <1.05 | 1:0.1600 |

A: Surf. D
B: 1135
Media: 1/10 TSB
Inoculum size: 1.16E+08

PPM AI MIC Values
(24 hrs)

| Test Organism | Alone | | Combination | | | Ratio |
|---|---|---|---|---|---|---|
| | CA | CB | Ca | Cb | S.I. | (Ca:Cb) |
| S. aureus ATCC#6538 | >20000 | 80 | 10000 | 50 | >1.13 | 1:0.0050 |
| | >20000 | 80 | 10000 | 60 | >1.25 | 1:0.0060 |
| | >20000 | 80 | 5000 | 50 | <0.88 | 1:0.0100 |

A: Surf. D
B: 1135
Media: 1/10 TSB
Inoculum size: 1.16E+08

PPM AI MIC Values
(24 hrs)

| Test Organism | Alone | | Combination | | | Ratio |
|---|---|---|---|---|---|---|
| | CA | CB | Ca | Cb | S.I. | (Ca:Cb) |
| | >20000 | 80 | 5000 | 60 | <1.00 | 1:0.0025 |
| | >20000 | 80 | 2500 | 60 | <0.88 | 1:0.0120 |
| | >20000 | 80 | 1750 | 50 | <0.71 | 1:0.0240 |
| | >20000 | 80 | 1750 | 60 | <0.84 | 1:0.0286 |
| | >20000 | 80 | 875 | 50 | <0.67 | 1:0.0343 |
| | >20000 | 80 | 875 | 60 | <0.79 | 1:0.0571 |
| | >20000 | 80 | 437.5 | 50 | <0.65 | 1:0.0686 |
| | >20000 | 80 | 437.5 | 60 | <0.77 | 1:0.1143 |
| | >20000 | 80 | 218.75 | 60 | <0.76 | 1:0.1371 |

A: Surf. E
B: DMO
Media: PDB
Inoculum size: 1.808E+06

PPM AI MIC Values
(48 hrs)

| Test Organism | Alone | | Combination | | | Ratio |
|---|---|---|---|---|---|---|
| | CA | CB | Ca | Cb | S.I. | (Ca:Cb) |
| C. albicans ATCC#10203 | >20000 | 1000 | 10000 | 600 | <1.10 | 1:0.0600 |
| | >20000 | 1000 | 10000 | 800 | <1.30 | 1:0.0800 |
| | >20000 | 1000 | 5000 | 600 | <0.85 | 1:0.1200 |
| | >20000 | 1000 | 5000 | 800 | <1.05 | 1:0.1600 |

A: Surf. E
B: DMO
Media: PDB

| P. aeruginosa | ATCC#15442 | No Synergy |
|---|---|---|

A: Surf. E
B: DMO
Media: PDB
Inoculum size: 1.56E+06 CFU/ml

PPM AI MIC Values
(3rd Day)

| Test Organism | Alone | | Combination | | | Ratio |
|---|---|---|---|---|---|---|
| | CA | CB | Ca | Cb | S.I. | (Ca:Cb) |
| A. niger ATCC#16404 | >20000 | 800 | 10000 | 600 | <1.25 | 1:0.0600 |
| | >20000 | 800 | 5000 | 600 | <1.00 | 1:0.1200 |
| | >20000 | 800 | 437.5 | 600 | <0.77 | 1:1.3714 |

| | A: Surf. E B: DMO Media: 1/10 TSB Inoculum size: 1.80E+06 CFU/ml | | | | | |
|---|---|---|---|---|---|---|
| | PPM AI MIC Values (24 hrs) | | | | | Ratio |
| Test | Alone | | Combination | | | |
| Organism | CA | CB | Ca | Cb | S.I. | (Ca:Cb) |
| ATCC# 6538 | >20000 | 80 | 10000 | 50 | <1.13 | 1:0.0050 |
| | >20000 | 80 | 10000 | 60 | <1.25 | 1:0.0060 |
| | >20000 | 80 | 5000 | 50 | <0.88 | 1:0.0100 |
| | >20000 | 80 | 5000 | 60 | <1.00 | 1:0.0120 |
| | >20000 | 80 | 2500 | 60 | <0.88 | 1:0.0240 |
| | >20000 | 80 | 1750 | 60 | <0.84 | 1:0.0343 |
| | >20000 | 80 | 875 | 60 | <0.79 | 1:0.0686 |
| | >20000 | 80 | 437.5 | 50 | <0.65 | 1:0.1143 |
| | >20000 | 80 | 437.5 | 60 | <0.77 | 1:0.1371 |
| | >20000 | 80 | 218.75 | 60 | <0.76 | 1:0.2743 |

The following biocides had no synergy against any organism tested when paired with the following surfactants:
Surf. A
Sodium Benzoate, TRIS NITRO
Surf. E
DMDMH
Surf. D
CS-1246, OPP, DMDMH
In the following combinations, the ratio of surfactant to biocide where synergy was observed were not commercially relevant, i.e., a ratio of 1:0.2 or greater (less biocide relative to surfactant). At these ratios, the biocide levels in a formulated product would be too low to be practical:
Surf. A
DIDAC, IPBC
Surf. E
CMIT/MIT, IPBC, OIT, TTPC, WSCP
Surf. D
CMIT/MIT, OIT, DIDAC
(MBIT, IPBC, WSCP were synergistic only at 1:0.05 or worse except for one data point)

The invention claimed is:

1. A synergistic microbicidal composition comprising: (a) a nonionic surfactant with structure:

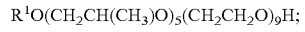

and (b) 4,4-dimethyloxazolidine; wherein a weight ratio of said nonionic surfactant to 4,4-dimethyloxazolidine is from 1:0.0286 to 1:0.1143 or 1:0.32 to 1:0.9143; and wherein $R^1$ is 2-ethylhexyl.

2. A synergistic microbicidal composition comprising: (a) a nonionic surfactant with structure:

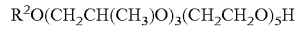

where $R^2$ is a mixture of $C_8$-$C_{14}$ linear alkyl groups; and (b) 4,4-dimethyloxazolidine; wherein a weight ratio of said nonionic surfactant to 4,4-dimethyloxazolidine is from 1:0.06 to 1:0.6857;
and wherein said mixture of $C_8$-$C_{14}$ linear alkyl groups comprises from 60 to 75 wt % $C_8$-$C_{10}$ linear alkyl groups and 25 to 40 wt % $C_{12}$-$C_{14}$ linear alkyl groups.

* * * * *